United States Patent [19]
Lemley, Jr. et al.

[11] Patent Number: 6,060,066
[45] Date of Patent: May 9, 2000

[54] METHOD FOR TREATING TUMORS WITH A TOXIN

[75] Inventors: Paul V. Lemley, Jr., Gettysburg, Pa.; Arthur E. Frankel, Charleston, S.C.

[73] Assignee: Novavax, Inc., Columbia, Md.

[21] Appl. No.: 08/897,090

[22] Filed: Jul. 18, 1997

Related U.S. Application Data

[62] Division of application No. 08/486,200, Jun. 7, 1995, Pat. No. 5,667,786.

[51] Int. Cl.$^7$ ..................................................... A61K 39/02
[52] U.S. Cl. ............................. 424/236.1; 514/2; 530/350
[58] Field of Search ................................. 530/350; 514/2; 424/236.1

[56] References Cited

PUBLICATIONS

Fodstad, O. et al. Cancers Res. 44:862–865, 1984.
Frankel et al. Oncology, 7(5):69–78, 1993.
Hewetson, JF et al. Vaccine 11(7):743–748, 1993.
Hewetson et al., *Vaccine*, "Protection of Mice From Inhaled Ricin by Vaccination With Ricin or by Passive Treatment with heterologous Antibody", vol. 11, Issue 7, pp. 743–746 (1993).
Rippy et al., *Soc. Tox. Path.*, "Immunization with Ricin Toxoid Prevents Death and Reduces Lung Injury", (1991), p. 10, (Abstract).
Lemley et al., Programme & Abstracts, Third Asia–Pacific Congress on Animal, Plant and Microbial Toxins, "Ricin Sub–Unit Vaccination in Mice and Protection from Challenge," p. B15, (Jun. 27–Jul. 1, 1993).
Lemley et al., *Hybridoma*, "Identification and Characterization of a Monoclonal Antibody that Neutralizes Ricin Toxicity in vitro and in vivo", vol. 13, No. 5, pp. 417–421 (1994).
Godal et al., *Int. J. Cancer,* "Antibody Formation Against the Cytotoxic Proteins Abrin and Ricin in Humans and Mice", vol. 32, pp. 515–521 (1983).
Lemley et al., 12th European Immunology Meeting, Barcelona Spain 1994 and 4th International Symposium on Immunotoxins, "Efficacy Characterization of Ricin Toxoid Vaccine in Mice", p. 6, (Abstract).
Lin et al., *J. Formosan Med. Assoc.*, "Antineoplastic Activity of Abrin", vol. 68, No. 11, pp. 567–568 (1969).
Hsu et al., *J. Formsan Med. Assoc.*, "Further Report on Therapeutic Effect of Abrin and Ricin on Human Cancers", vol. 73, pp. 526–542 (1974).
Osband et al., "Problems in the Investigational Study and Clinical use of Cancer Immunotherapy", Immunotherapy Today, vol. 11, pp. 193–195, 1990.
Hewetson et al., "A Formalinized Toxoid for Protection of Mice from Inhaled Ricin", Vaccine Research, vol. 4, No. 4, pp. 179–187, 1995.

*Primary Examiner*—Paula K. Hutzell
*Assistant Examiner*—Minh-Tam Davis
*Attorney, Agent, or Firm*—Lahive & Cockfield, LLP

[57] ABSTRACT

A method for treating a tumor is provided, which comprises the steps of preliminarily immunizing a patient in need of antitumor treatment with a toxin or toxin surrogate vaccine in an amount which is effective to generate an immune response to the toxin in the patient, thereby providing systemic protection from the toxin to the patient, and subsequently administering the toxin to the patient in an amount which is effective to kill tumor cells. The toxin may be any suitable toxin, for example ricin, abrin, gelonin or diphtheria.

4 Claims, No Drawings

METHOD FOR TREATING TUMORS WITH A TOXIN

This is a divisional application of Ser. No. 08/486,200, filed Jun. 7, 1995 now U.S. Pat. No. 5,667,786.

BACKGROUND OF THE INVENTION

1. Field of the Invention

The instant invention is a novel method for treating tumors with a toxin. More specifically, the present method involves preliminarily immunizing a patient with a toxin vaccine containing a cytotoxic cancerostatic toxin or toxin surrogate to generate an immune response to the toxin in the patient and to thereby provide systemic protection from the toxin in the patient, and then administering the cytotoxic cancerostatic toxin to the patient to directly treat the tumor.

2. Description of Related Art

Various methods for treating tumors using toxins have been known and are presently under investigation. The most common of these methods is immunotoxin therapy, which involves administering to a cancer patient usually by systemic infusion a toxin linked to a peptide ligand. The ligand portion of the immunotoxin is usually an antibody or hormone. The ligand of the immunotoxin directs the molecule to the surface of the tumor cell, where the toxin enters the cell to kill the cell. Most toxins work by inactivating the cell ribosomes, thereby stopping protein synthesis in the cell. See, e.g., Oncology, "Immunotoxin Therapy of Cancer", May 1993.

While effective in some cases, several problems have been recognized with immunotoxin therapy, making it clear that immunotoxin therapy is not, at least so far, the "silver bullet" for cancer treatment that it was once hoped to be.

One problem with immunotoxin therapy is that the large size of the immunotoxin molecules and the poor vasculature of most tumors leads to a high intravascular drug concentration but a low drug concentration in the tumor interstitia. Consequently, toxicities to accessible normal tissues is high, while efficacy is poor. For example, immunotoxins have been found to react with neural and hepatic tissue antigens and produce serious, and sometimes fatal, toxicities.

Another problem with immunotoxins is that they are significantly immunogenic, generating humoral immune responses to the molecule. The resulting immune complexes of antibody-immunotoxin reduce the effective level of immunotoxin systemically by, for example, inhibiting the internalization of the immunotoxin into the tumor cell.

A second known method for treating tumors with a toxin involves the intravenous treatment of a tumor using a sub-lethal dose of the toxin. This treatment, about which there is only one report known to the present inventors, demonstrated an antitumor effect of the toxin in human clinical trials, but the patients had adverse side effects at high doses. In addition, since toxins are notably immunogenic, the patients mounted an immune response to the toxin which eventually abrogated any effect of the treatment.

Most notably, the above report on the clinical experiment concluded that intravenous treatment of a tumor with a toxin suffered from a problem of having a limited duration of effective therapy. The report concluded that the therapy becomes ineffective when antibody titers to the toxin in the patient reach a concentration sufficient to counteract or abolish the antitumor effect of the toxin. See Godal et al., Int J. Cancer, "Antibody Formation Against the Cytotoxic Proteins Abrin and Ricin in Humans and Mice", Vol. 32, pp 515–521 (1983).

SUMMARY OF THE INVENTION

It is an object of the invention to provide an improved method for intravenous treatment of a tumor with a toxin.

More specifically, it is an object of the invention to minimize the side effects produced in patients from the toxin to be administered.

It is a further object of the invention to extend the duration of effective toxin therapy, curtailed in present methods by the immune response mounted to the toxin which is considered to eventually abrogate any effect of the treatment.

It is a still further object of the invention to avoid the problem of immunotoxin therapy in having a low drug concentration at the tumor site.

The present invention has been achieved by the discovery by the present inventors that the afore-mentioned problems can be solved by preliminarily immunizing the patient with the toxin or toxin surrogate as a vaccine. As with conventional vaccines, the toxin vaccine provokes an immune response which is sufficient to provide systemic protection to the patient. It is then possible to directly treat the tumor with the toxin, for example by direct intratumoral injection of lethal doses of the toxin into the tumor. The systemic protection of the patient against the toxin protects the normal tissues of the patient from any toxin which might escape from the tumor.

Thus, in contrast to the intravenous treatment method mentioned above which considered the development of the patient's immune response to the toxin to be a disadvantage, the present invention turns the immune response into an asset for the treatment of tumors.

To the knowledge of the present inventors, the antitumor treatment method of the present invention characterized by a pre-immunization of the tumor patient with a toxin vaccine to develop a systemic immunity to the toxin, before administering the toxin to directly kill the tumor cells, is entirely novel and unsuggested in the prior art.

The present invention will now be explained in more detail hereinbelow.

DETAILED DESCRIPTION OF THE PREFERRED EMBODIMENT(S)

The present method is suitable for treating tumors in humans, non-human mammals (monkey, mouse, etc.), pets (dog, cat, hamster, etc.), livestock (cow, horse, pig, sheep, goat, etc), and zoo animals (elephant, giraffe, etc.).

The present method is suitable for treating both solid tumors (liver, pancreas, breast, brain, lung, head, neck, etc.) and non-solid tumors (leukemia, B-cell lymphoma, etc.). Treatment of solid tumors is particularly preferred.

The toxins which are useful in the method of the present invention are generally any known cytotoxic cancerostatic protein toxins. Ricin, abrin, gelonin, exotoxin A and diphtheria are preferred.

Systemic protection from the toxin in the patient is achieved by an active immunization of the patient with a sub-lethal dose of the whole toxin, or a toxin surrogate. The term toxin surrogate means a sub-unit or portion of the toxin capable of stimulating the immune response, or a toxoid derivative of the toxin.

It is known in the art that an active protective immune response can be achieved by sub-lethal doses of a toxin (Hewetson et al., *Vaccine*, "Protection of mice from inhaled ricin by vaccination with ricin or by passive treatment with heterologous antibody", Vol. 11, Issue 7, 1993; Godal et al., *Int. J. Cancer*, cited above), a toxoid (Rippy et al., *Soc. Tox. Path.*, 1991) or sub-units of a toxin (Lemley et al., Programme and Abstracts, Third Asia-Pacific Congress on Animal, Plant and Microbial Toxins, Jun. 27–Jul. 1, 1993).

The whole toxin or sub-units of the toxin can be obtained from commercial sources, such as from Inland Laboratories, Austin, Tex., and diluted in a pharmaceutically acceptable carrier. Sub-units of the toxin can be prepared by known methods from the whole toxin.

A toxoid preparation of the toxin can be prepared by conventional methods, such as by stirring with formaldehyde (10% formaldehyde which is 3.7% formalin in phosphate buffered saline) for 28 days at 4° C. followed by extensive dialysis against phosphate buffered saline.

Formalin inactivation of whole ricin can be achieved by incubating with formaldehyde for 3 days followed by stationary phase, surface to air evaporation to precipitate the vaccine is described on page 418 of Lemley et al., *Hybridoma*, "Identification and Characterization of a Monoclonal Antibody that Neutralizes Ricin Toxicity In Vitro and In Vivo", Vol. 13, No. 5, 1994.

Licensed vaccines of some toxins, for example diphtheria, are commercially available. Methods for preparing vaccines and generating antibodies are also known in the art. For example, methods for generating antibodies to diphtheria in humans and mice are also described in Godal et al., *Int. J. Cancer*, cited above.

To achieve systemic protection, the amount of the toxin or toxin surrogate to be administered the patient is in the range from 1.0–1,000 μg/dose. A 5.0–10.0 μg/dose is preferred. These dosage ranges apply to generally all known toxins and routes of administration. The dosage ranges also generally apply to any potential patient regardless of weight. Thus, the amount of toxin to be administered a mouse can be about 5.0 μg/dose, while the amount of toxin to administer to a human can be about 10.0 μg/dose.

One skilled in the art can readily determine the optimal dosage of toxin or toxin surrogate to administer to a patient to achieve systemic protection using known methods. For example, the optimal dosage may be determined by conducting a clinical trial administering escalating dosages of the toxin beginning at the lower dosage range to determine a dosage which affords the desired level of systemic protection. Systemic protection can be evaluated standard methods, such as ELISA (titer >300), cell assay or by neutralizing the toxin with sera and injecting into naive mice.

The toxin may be optionally administered with a conventional adjuvant to enhance the immune response. Only alum is presently approved for use in humans as an adjuvant. For animal uses, a plurality of adjuvants are approved and may be used.

The toxin or toxin surrogate vaccine is administered by any conventional route for administering vaccines. Intramuscular, subcutaneous, oral, topical, mucosal and aerosol are preferred.

The minimum effective amount of toxin to achieve systemic protection is a single dose of about 10.0 μg of formalin treated toxin/alum absorbed.

In the most preferred embodiment, the patient is immunized with the toxin vaccine, including an adjuvant, in a single intramuscular injection, or 2–3 i.m. injections, of 5.0–10.0 μg. In the case of multiple dosages, the dosages are preferably given two weeks apart. In the case of a single dosage, the first toxin treatment can operate as a booster.

Direct treatment of the tumor with the toxin is begun preferably about two weeks after immunization. The toxin must be the same toxin used in the immunization step.

Whole toxin is preferably administered in most cases, not a toxin surrogate, although an active derivative or portion of the whole toxin might be used if the molecule is cytotoxic and cancerostatic.

The toxin can be administered in any acceptable pharmaceutical medium. The toxin is usually administered in a sterile saline solution. The toxin may optionally contain a known protein stabilizing agent which is not immunogenic, such as human albumin in the case of treating human patients.

The toxin may be administered to the patient through any conventional route. An intratumoral delivery of the toxin directly into the tumor is preferred, achieved by infusion or catheter. In the case of the intravenous injection of the toxin, the systemic protection of the patient is expected to protect the normal tissues from the toxin while killing the tumor cells having a faster growth rate rendering the tumor cells more susceptible to the toxin.

The toxin is administered in as many dosages as the patient can tolerate and as necessary to achieve an antitumor effect. Preferably one or two doses of toxin are administered.

To achieve an antitumor effect, the amount of the toxin to be administered the patient is in the range from 100 μg–1.0 mg per dose. A dose of 5.0–10.0 μg/dose is preferred. These dosage ranges apply to generally all known toxins and routes of administration. The dosage ranges also generally apply to any patient regardless of weight.

In the most preferred embodiment, the toxin is administered by intratumoral infusion or catheter in an amount of 10 to 100 times the lethal dose for the patient.

One skilled in the art can readily determine the optimal dosage of toxin to administer to a patient to achieve an antitumor effect using known methods, for example those methods used in treatment methods using known toxins discussed above, and those methods using other cytotoxic antitumor agents such as chemotherapeutic agents and ethanol. The optimal dosage may be determined by conducting a clinical trial using escalating dosages of the toxin beginning at the lower dosage range to determine a dosage of toxin which the patient can tolerate while achieving an antitumor effect.

The method of the present invention also has the advantage of being inexpensive, at least from the standpoint of the vaccine and toxin used. The cost of the vaccines is estimated to be in the range of $1.00–$5.00 per dose. The cost of the therapeutic toxin in a dose of 100 μg–1.0 mg is estimated to be $20–$25/mg.

Hence, the pharmaceuticals used in the method of the present invention procedure are very inexpensive, making the therapy quite feasible for zoo animals, pets or livestock, as well as humans.

The present invention also includes a toxin or toxin surrogate vaccine, as described above, and a kit containing a vial or unit containing the toxin or toxin surrogate vaccine together with a vial or unit containing the toxin treatment.

We claim:

1. A kit for treating a tumor, which comprises a first unit containing a toxin or a toxin surrogate vaccine in an amount which is effective to generate an immune response to the toxin in a patient, thereby providing systemic protection from the toxin, and a second unit containing the toxin in an amount which is effective to kill tumor cells, said vaccine comprising ricin toxoid and adjuvant, and said second unit comprising a tumor-killing effective amount of ricin in sterile saline.

2. A kit for carrying out a method of treating tumors, which comprises a first unit containing an adjuvant, and a toxin or toxin surrogate vaccine in an amount that generates an immune response to the toxin in a patient, thereby providing systemic protection from the toxin, and a second unit containing the corresponding toxin in the amount which is effective to kill tumor cells, said vaccine selected from the group consisting of a ricin toxoid and a ricin-a-chain, and said second unit further containing sterile saline.

3. The kit according to claim 2, which contains a unit containing a vaccine of ricin toxoid, an adjuvant, and a unit containing a tumor-killing effective amount of ricin in sterile saline.

4. The kit according to claim 2, which contains a unit containing a vaccine of ricin a-chain, an adjuvant, and a unit containing a tumor-killing effective amount of the ricin in sterile saline.

* * * * *